US012788466B2

(12) United States Patent
Johnson et al.

(10) Patent No.: US 12,788,466 B2
(45) Date of Patent: Nov. 10, 2026

(54) METHODS AND ABLATION SYSTEMS FOR TREATMENT OF SACROILIAC JOINT PAIN USING SHORT, HIGH VOLTAGE PULSES

(71) Applicant: Boston Scientific Neuromodulation Corporation, Valencia, CA (US)

(72) Inventors: Courtney Johnson, Valencia, CA (US); Brendan Early Koop, Ham Lake, MN (US); Michael Sean Coe, Plymouth, MN (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 191 days.

(21) Appl. No.: 18/747,174

(22) Filed: Jun. 18, 2024

(65) Prior Publication Data

US 2024/0423687 A1 Dec. 26, 2024

Related U.S. Application Data

(60) Provisional application No. 63/522,372, filed on Jun. 21, 2023.

(51) Int. Cl.
*A61B 18/00* (2006.01)

(52) U.S. Cl.
CPC .... *A61B 18/00* (2013.01); *A61B 2018/00083* (2013.01); *A61B 2018/0044* (2013.01);
(Continued)

(58) Field of Classification Search
CPC ................ A61B 18/00; A61B 18/1477; A61B 2018/00083; A61B 2018/0044;
(Continued)

(56) References Cited

U.S. PATENT DOCUMENTS 4,411,266 A 10/1983 Cosman
4,565,200 A 1/1986 Cosman
(Continued)

FOREIGN PATENT DOCUMENTS

WO 99/40859 8/1999
WO 99/40860 8/1999
(Continued)

OTHER PUBLICATIONS

Hemostasis Vales—Qosina—URL: hllps://www.qosina.com/vascular-access-hemostasis-valves 9 pages—retrieved Nov. 13, 2019.
(Continued)

*Primary Examiner* — Khadijeh A Vahdat
(74) *Attorney, Agent, or Firm* — Branch Partners PLLC; Bruce E. Black

(57) ABSTRACT

A method to treat sacroiliac joint pain includes inserting at least one ablation electrode into a patient to ablate at least one spinal nerve extending from the spinal cord in the vertebral range of the lumbar vertebrae L3, L4, or L5 or any of the sacral vertebrae; and applying pulses to the at least one ablation electrode to ablate the at least one nerve, wherein each of the pulses has a duration of no more than 500 microseconds and at least some of the pulses have a voltage of at least 1 kV or generate an electric field of at least 3 kV/cm.

20 Claims, 3 Drawing Sheets

(52) U.S. Cl.
CPC ............... *A61B 2018/00577* (2013.01); *A61B 2018/00613* (2013.01); *A61B 2018/00761* (2013.01); *A61B 2018/00767* (2013.01)

(58) Field of Classification Search
CPC ........... A61B 2018/00577; A61B 2018/00613; A61B 2018/00702; A61B 2018/00761; A61B 2018/00767; A61B 2018/1467
See application file for complete search history.

(56) References Cited

U.S. PATENT DOCUMENTS

| | | | |
|---|---|---|---|
| 4,566,454 | A | 1/1986 | Mehl et al. |
| 4,597,379 | A | 7/1986 | Kihn et al. |
| 4,727,874 | A | 3/1988 | Bowers et al. |
| 4,807,620 | A | 2/1989 | Strul et al. |
| 5,360,009 | A | 11/1994 | Herskovitz |
| 5,433,739 | A | 7/1995 | Sluijter et al. |
| 5,571,147 | A | 11/1996 | Sluijter et al. |
| 5,728,143 | A | 3/1998 | Gough et al. |
| 5,769,847 | A | 6/1998 | Panescu et al. |
| 5,951,546 | A | 9/1999 | Lorentzen |
| 5,983,141 | A | 11/1999 | Sluijter et al. |
| 6,070,845 | A | 6/2000 | Herskovitz |
| 6,080,149 | A | 6/2000 | Huang et al. |
| 6,104,959 | A | 8/2000 | Spertell |
| 6,161,048 | A | 12/2000 | Sluijter et al. |
| 6,203,524 | B1 | 3/2001 | Burney et al. |
| 6,245,065 | B1 | 6/2001 | Panescu et al. |
| 6,246,912 | B1 | 6/2001 | Sluijter et al. |
| 6,259,952 | B1 | 7/2001 | Sluijter et al. |
| 6,301,506 | B1 | 10/2001 | Den Boer et al. |
| 6,321,120 | B1 | 11/2001 | Surbeck et al. |
| 6,341,429 | B1 | 1/2002 | Herskovitz |
| 6,397,106 | B1 | 5/2002 | DeBrouse |
| 6,402,739 | B1 | 6/2002 | Neev |
| 6,428,537 | B1 | 8/2002 | Swanson et al. |
| 6,440,127 | B2 | 8/2002 | McGovern et al. |
| 6,447,505 | B2 | 9/2002 | McGovern et al. |
| 6,482,204 | B1 | 11/2002 | Lax et al. |
| 6,517,534 | B1 | 2/2003 | McGovern et al. |
| 6,530,922 | B2 | 3/2003 | Cosman et al. |
| 6,692,493 | B2 | 2/2004 | McGovern et al. |
| 6,743,226 | B2 | 6/2004 | Cosman et al. |
| 6,843,789 | B2 | 1/2005 | Goble |
| 6,853,864 | B2 | 2/2005 | Litovitz |
| 6,869,430 | B2 | 3/2005 | Balbierz et al. |
| 7,363,071 | B2 | 4/2008 | Damasco et al. |
| 7,522,953 | B2 | 4/2009 | Kaula et al. |
| 7,553,309 | B2 | 6/2009 | Buysse et al. |
| 7,574,257 | B2 | 8/2009 | Rittman, III |
| 7,725,155 | B2 | 5/2010 | Dowlatshahi |
| 7,749,218 | B2 | 7/2010 | Pellegrino et al. |
| 7,799,024 | B2 | 9/2010 | Randall |
| 7,945,331 | B2 * | 5/2011 | Vilims .................. A61N 1/403 607/46 |
| 8,123,782 | B2 | 2/2012 | Altarac et al. |
| 8,128,662 | B2 | 3/2012 | Altarac et al. |
| 8,273,108 | B2 | 9/2012 | Altarac et al. |
| 8,277,488 | B2 | 10/2012 | Altarac et al. |
| 8,292,922 | B2 | 10/2012 | Altarac et al. |
| 8,361,607 | B2 | 1/2013 | Higuchi et al. |
| 8,425,559 | B2 | 4/2013 | Tebbe et al. |
| 8,512,333 | B2 | 8/2013 | Epstein et al. |
| 8,518,037 | B2 | 8/2013 | Young |
| 8,613,747 | B2 | 12/2013 | Altarac et al. |
| 8,808,284 | B2 | 8/2014 | Pellegrino et al. |
| 8,864,828 | B2 | 10/2014 | Altarac et al. |
| 8,945,183 | B2 | 2/2015 | Altarac et al. |
| 8,979,830 | B2 | 3/2015 | Hennings |
| 8,992,522 | B2 | 3/2015 | Pellegrino et al. |
| 9,039,701 | B2 | 5/2015 | Pellegrino et al. |
| 9,119,680 | B2 | 9/2015 | Altarac et al. |
| 9,155,570 | B2 | 10/2015 | Altarac et al. |
| 9,155,572 | B2 | 10/2015 | Altarac et al. |
| 9,161,783 | B2 | 10/2015 | Altarac et al. |
| 9,173,676 | B2 | 11/2015 | Pellegrino et al. |
| 9,186,186 | B2 | 11/2015 | Reglos et al. |
| 9,393,055 | B2 | 7/2016 | Altarac et al. |
| 9,532,812 | B2 | 1/2017 | Altarac et al. |
| 9,572,603 | B2 | 2/2017 | Altarac et al. |
| 9,717,552 | B2 | 8/2017 | Cosman et al. |
| 9,861,398 | B2 | 1/2018 | Altarac et al. |
| 9,949,782 | B2 | 4/2018 | Hagg et al. |
| 9,956,011 | B2 | 5/2018 | Altarac et al. |
| 9,956,032 | B1 | 5/2018 | Cosman et al. |
| 10,080,587 | B2 | 9/2018 | Altarac et al. |
| 10,111,703 | B2 | 10/2018 | Cosman, Jr. et al. |
| 10,136,937 | B1 | 11/2018 | Cosman, Jr. et al. |
| 10,136,942 | B1 | 11/2018 | Cosman, Jr. et al. |
| 10,136,943 | B1 | 11/2018 | Cosman, Jr. et al. |
| 10,166,047 | B2 | 1/2019 | Altarac et al. |
| 10,194,971 | B2 | 2/2019 | Wegrzyn, III et al. |
| 10,342,606 | B2 | 7/2019 | Cosman et al. |
| 10,357,258 | B2 | 7/2019 | Patel et al. |
| 10,363,063 | B2 | 7/2019 | Cosman |
| 10,420,591 | B2 | 9/2019 | Snell et al. |
| 10,463,423 | B2 | 11/2019 | Sutton et al. |
| 10,478,246 | B2 | 11/2019 | Pellegrino et al. |
| 10,517,611 | B2 | 12/2019 | Patel et al. |
| 10,548,654 | B2 | 2/2020 | Curley |
| 10,588,687 | B2 | 3/2020 | Cosman, Jr. et al. |
| 10,610,267 | B2 | 4/2020 | Altarac et al. |
| 10,631,915 | B1 | 4/2020 | Cosman |
| 10,639,098 | B2 | 5/2020 | Cosman et al. |
| 10,639,101 | B2 | 5/2020 | Cosman et al. |
| 10,653,456 | B2 | 5/2020 | Altarac et al. |
| 10,709,502 | B2 | 7/2020 | Viswanathan |
| 10,835,295 | B2 | 11/2020 | Altarac et al. |
| 10,835,297 | B2 | 11/2020 | Altarac et al. |
| 11,013,539 | B2 | 5/2021 | Altarac et al. |
| 11,058,455 | B2 | 7/2021 | Cosman, Jr. |
| 11,076,893 | B2 | 8/2021 | Altarac et al. |
| 11,116,585 | B2 | 9/2021 | Lyons et al. |
| 11,207,100 | B2 | 12/2021 | Donovan et al. |
| 11,229,461 | B2 | 1/2022 | Altarac et al. |
| 2002/0077683 | A1 | 6/2002 | Westlund et al. |
| 2002/0156472 | A1 | 10/2002 | Lee et al. |
| 2002/0165531 | A1 | 11/2002 | Goble |
| 2003/0032951 | A1 | 2/2003 | Rittman et al. |
| 2003/0212390 | A1 | 11/2003 | Chen et al. |
| 2005/0065509 | A1 | 3/2005 | Coldwell et al. |
| 2005/0277918 | A1 | 12/2005 | Shah et al. |
| 2006/0052850 | A1 | 3/2006 | Darmos et al. |
| 2007/0032835 | A1 | 2/2007 | Rittman |
| 2008/0195152 | A1 | 8/2008 | Altarac et al. |
| 2008/0200972 | A1 | 8/2008 | Rittman et al. |
| 2008/0262490 | A1 | 10/2008 | Williams |
| 2009/0138046 | A1 | 5/2009 | Altarac et al. |
| 2010/0114093 | A1 | 5/2010 | Mahapatra et al. |
| 2010/0222747 | A1 | 9/2010 | Wenchell et al. |
| 2010/0249750 | A1 | 9/2010 | Racz et al. |
| 2011/0028836 | A1 | 2/2011 | Ranpura et al. |
| 2011/0288540 | A1 | 11/2011 | Wright et al. |
| 2011/0301578 | A1 | 12/2011 | Muniz-Medina et al. |
| 2012/0203064 | A1 | 8/2012 | Wynberg |
| 2012/0215218 | A1 * | 8/2012 | Lipani .................. A61N 1/0551 606/41 |
| 2012/0310230 | A1 * | 12/2012 | Willis .................... A61N 1/327 606/41 |
| 2013/0345699 | A1 | 12/2013 | Brannan et al. |
| 2014/0066917 | A1 | 3/2014 | Cosman, Jr. et al. |
| 2014/0081260 | A1 | 3/2014 | Cosman, Jr. et al. |
| 2014/0121658 | A1 | 5/2014 | Cosman, Jr. et al. |
| 2014/0276800 | A1 | 9/2014 | Batchelor et al. |
| 2015/0182234 | A1 | 7/2015 | Mahoney et al. |
| 2015/0297282 | A1 | 10/2015 | Cadouri |
| 2015/0305799 | A1 | 10/2015 | Trieu |
| 2016/0206362 | A1 | 7/2016 | Mehta et al. |
| 2016/0242822 | A1 | 8/2016 | Altarac et al. |
| 2016/0278791 | A1 | 9/2016 | Pellegrino et al. |
| 2016/0310211 | A1 * | 10/2016 | Long .................. A61B 18/1492 |
| 2017/0004951 | A1 | 1/2017 | Weisz et al. |
| 2017/0049514 | A1 | 2/2017 | Cosman |

(56) References Cited

U.S. PATENT DOCUMENTS

| | | | |
|---|---|---|---|
| 2018/0161086 A1* | 6/2018 | Davalos | A61N 1/327 |
| 2018/0318061 A1 | 11/2018 | Clarke et al. | |
| 2019/0110833 A1 | 4/2019 | Pellegrino et al. | |
| 2019/0201057 A1 | 7/2019 | Altarac et al. | |
| 2019/0223948 A1 | 7/2019 | Stewart et al. | |
| 2019/0239941 A1 | 8/2019 | Schorr et al. | |
| 2020/0038091 A1 | 2/2020 | Cao et al. | |
| 2020/0038096 A1 | 2/2020 | Schepis et al. | |
| 2020/0139144 A1 | 5/2020 | Cosman et al. | |
| 2020/0146744 A1 | 5/2020 | Defosset et al. | |
| 2020/0147371 A1* | 5/2020 | Pakhomov | A61B 18/14 |
| 2020/0205892 A1* | 7/2020 | Viswanathan | A61B 18/1492 |
| 2020/0281646 A1 | 9/2020 | Pellegrino et al. | |
| 2020/0330153 A1 | 10/2020 | Cosman, Jr. et al. | |
| 2020/0383707 A1 | 12/2020 | Kidman et al. | |
| 2021/0038298 A1 | 2/2021 | Scott et al. | |
| 2021/0100592 A1 | 4/2021 | Seifert et al. | |
| 2021/0113239 A1* | 4/2021 | Donovan | A61B 17/3423 |
| 2021/0121224 A1 | 4/2021 | Ranpura et al. | |
| 2021/0236191 A1 | 8/2021 | Wang et al. | |
| 2021/0322063 A1 | 10/2021 | Altarac et al. | |
| 2021/0369394 A1 | 12/2021 | Braido et al. | |
| 2021/0393315 A1 | 12/2021 | McGregor et al. | |
| 2022/0061894 A1 | 3/2022 | Altarac et al. | |
| 2022/0202484 A1 | 6/2022 | Wang et al. | |
| 2022/0202485 A1 | 6/2022 | Marusich et al. | |
| 2022/0226039 A1 | 7/2022 | Wang | |
| 2022/0323147 A1 | 10/2022 | Hata et al. | |
| 2022/0401085 A1 | 12/2022 | Cosman, Jr. | |
| 2024/0108361 A1 | 4/2024 | Johnson et al. | |
| 2024/0108394 A1 | 4/2024 | Bates et al. | |
| 2024/0245445 A1 | 7/2024 | Bates | |
| 2024/0245449 A1 | 7/2024 | Bates | |
| 2024/0277384 A1 | 8/2024 | Malinowski | |
| 2024/0423701 A1 | 12/2024 | Johnson et al. | |

FOREIGN PATENT DOCUMENTS

| | | |
|---|---|---|
| WO | 00/59394 | 10/2000 |
| WO | 2007121143 | 10/2007 |
| WO | 2014130031 | 8/2014 |
| WO | WO2022011115 | 1/2022 |

OTHER PUBLICATIONS

*Coolief* Cooled Radio Frequency Kit—Instructions for Use Halyard—dated Feb. 9, 2017—8 pages.

Cobra R-F™—Epimed—URL: https://www.epimed.com/products/cobra-r-f/—retrieved Jan. 27, 2021.

Hyso et al., "Epimed Launches "Cobra" R-F™ Dual Use Radiofrequency Cannula" Cision—PR Web—Jan. 17, 2019 3 pages.

"Venom cannula and electrode system"—Stryker—retrieved Sep. 8, 2020 URL: https://www.stryker.com/us/en/interventional-spine/products/venom-cannula-and-electrode-system.html.

"RF Trident™ Cannulae" Diros Technology Inc. Nov. 11, 2017 URL: https://web.archive.org/web/20171117054945/https://dirostech.com/product-details/rf-tridenttrident-hybrid-cannulae/.

Cedeno et al., "Comparisons of Lesion Volumes and Shapes Produced by a Radiofrequency System with a Cooled, a Protruding, or a Monopolar Probe" Pain Physician 2017; 20:E915-E922 • ISSN 2150-1149.

Correspondence from Department of Health and Human Services to George Darmos at Diros Technology, Inc.—dated Jul. 30, 2015—11 pages.

Correspondence from Department of Health and Human Services to Christina McKee—dated Mar. 28, 2013; 7 pages.

Cosman et al. "Theoretical Aspects of Radiofrequency Lesions in the Dorsal Root Entry Zone," Neurosurgery, vol. 15, No. 6, p. 945-950 (1984).

Todorov L. Pulsed radiofrequency of the sural nerve for the treatment of chronic ankle pain. Pain Physician. May-Jun. 2011;14(3):301-4. PMID: 21587334.

Rhame EE, Levey KA, Gharibo CG. Successful treatment of refractory pudendal neuralgia with pulsed radiofrequency. Pain Physician. May-Jun. 2009;12(3):633-8. PMID: 19461829.

U.S. Appl. No. 63/522,367, filed Jun. 21, 2023.

Declaration of Non-Establishment of International Search Report and Written Opinion for PCT Application No. PCT/US2024/034536 mailed Sep. 26, 2024.

* cited by examiner

METHODS AND ABLATION SYSTEMS FOR TREATMENT OF SACROILIAC JOINT PAIN USING SHORT, HIGH VOLTAGE PULSES

CROSS-REFERENCE TO RELATED APPLICATIONS

This application claims the benefit under 35 U.S.C. § 119 (e) of U.S. Provisional Patent Application Ser. No. 63/522,372, filed Jun. 21, 2023, which is incorporated herein by reference.

FIELD

The present disclosure is directed to the area of ablation systems and methods of making and using the systems. The present disclosure is also directed to systems and methods of treatment for sacroiliac (SI) joint pain by nerve ablation using short, high voltage pulses.

BACKGROUND

Ablation generators and electrodes can be used for pain relief or functional modification. Ablation can be used to treat cardiac arrhythmias, benign tumors, cancerous tumors, and to control bleeding during surgery. Ablation is a safe, proven means of interrupting pain signals, such as those coming from irritated facet joints in the spine, genicular nerves in the knee, and femoral and obturator nerves in the hip. There is a need for new ablation treatments to address pain and other disorders.

BRIEF SUMMARY

One aspect is a method to treat sacroiliac joint pain. The method includes inserting at least one ablation electrode into a patient to ablate at least one spinal nerve extending from the spinal cord in the vertebral range of the lumbar vertebrae L3, L4, or L5 or any of the sacral vertebrae; and applying pulses to the at least one ablation electrode to ablate the at least one nerve, wherein each of the pulses has a duration of no more than 500 microseconds and at least some of the pulses have a voltage of at least 1 kV.

Another aspect is a system for treating sacroiliac joint pain. The system includes a memory having instructions stored thereon and a processor configured to execute those instructions to perform actions including applying pulses to at least one ablation electrode to ablate at least one spinal nerve extending from the spinal cord in the vertebral range of the lumbar vertebrae L3, L4, or L5 or any of the sacral vertebrae, wherein each of the pulses has a duration of no more than 500 microseconds and at least some of the pulses have a voltage of at least 1 kV.

A further aspect is a non-transitory computer-readable medium having stored thereon instructions for treating sacroiliac joint pain, wherein the instructions, when executed by a processor, perform actions including applying pulses to at least one ablation electrode to ablate at least one spinal nerve extending from the spinal cord in the vertebral range of the lumbar vertebrae L3, L4, or L5 or any of the sacral vertebrae, wherein each of the pulses has a duration of no more than 500 microseconds and at least some of the pulses have a voltage of at least 1 kV.

In at least some aspects, the at least one spinal nerve includes at least one sacral lateral branch nerve. In at least some aspects, each of the pulses has a voltage of at least 2 kV. In at least some aspects, each of the pulses has a voltage of at least 3 kV. In at least some aspects, at least a plurality of the pulses each have a duration of no more than 100 microseconds. In at least some aspects, at least a plurality of the pulses are separated from each other by no more than 20 milliseconds.

In at least some aspects, the pulses are arranged in a plurality of pulse bursts, wherein each of the pulse bursts includes a plurality of the pulses, wherein the pulse bursts are separated from each other by at least 3 microseconds. In at least some aspects, the pulses are monophasic. In at least some aspects, the pulses are multiphasic.

In at least some aspects, the at least one nerve includes a plurality of the nerves and inserting the at least one ablation electrode includes inserting the at least one ablation electrode at different positions along the plurality of the nerves. In at least some aspects, the at least one ablation electrode includes at least one multipolar ablation electrode.

In at least some aspects, the at least one ablation electrode includes a plurality of monoelectrode ablation electrodes. In at least some aspects, applying the pulses includes applying the pulses to at least one set of the monoelectrode ablation electrodes, wherein each of the at least one set includes at least one first monoelectrode ablation electrode that is an active electrode and at least one second monoelectrode ablation electrode that is a return electrode.

Another aspect is a method to treat sacroiliac joint pain. The method includes inserting at least one ablation electrode into a patient to ablate at least one spinal nerve extending from the spinal cord in the vertebral range of the sacral vertebrae or the lumbar vertebrae L3, L4, or L5; and applying pulses to the at least one ablation electrode to ablate the at least one nerve, wherein each of the pulses has a duration of no more than 500 microseconds and at least some of the pulses generate an electric field of at least 3 kV/cm.

Another aspect is a system for treating sacroiliac joint pain. The system includes a memory having instructions stored thereon and a processor configured to execute those instructions to perform actions including applying pulses to at least one ablation electrode to ablate at least one spinal nerve extending from the spinal cord in the vertebral range of the sacral vertebrae or the lumbar vertebrae L3, L4, or L5, wherein each of the pulses has a duration of no more than 500 microseconds and at least some of the pulses generate an electric field of at least 3 kV/cm.

A further aspect is a non-transitory computer-readable medium having stored thereon instructions for treating sacroiliac joint pain, wherein the instructions, when executed by a processor, perform actions including applying pulses to at least one ablation electrode to ablate at least one spinal nerve extending from the spinal cord in the vertebral range of the sacral vertebrae or the lumbar vertebrae L3, L4, or L5, wherein each of the pulses has a duration of no more than 500 microseconds and at least some of the pulses generate an electric field of at least 3 kV/cm.

In at least some aspects, each of the pulses generates an electric field of at least 3.5 kV/cm. In at least some aspects, at least a plurality of the pulses each have a duration of no more than 100 microseconds. In at least some aspects, at least a plurality of the pulses are separated from each other by no more than 20 milliseconds.

In at least some aspects, the plurality of ablation electrodes includes a plurality of monoelectrode ablation electrodes. In at least some aspects, applying the pulses includes applying the pulses to at least one set of the monoelectrode ablation electrodes, wherein each of the at least one set includes at least one first monoelectrode ablation electrode that is an active electrode and at least one second monoelectrode ablation electrode that is a return electrode.

In at least some aspects, the plurality of ablation electrodes includes at least one multipolar ablation electrode including a plurality of the ablation electrodes.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present disclosure is directed to the area of ablation systems and methods of making and using the systems. The present disclosure is also directed to systems and methods of treatment for sacroiliac (SI) joint pain by nerve ablation using short, high voltage pulses.

Many conventional ablation generators for pain management support one or more monopolar ablation electrodes with each monopolar ablation electrode having one conductor. A temperature measurement device, such as a thermocouple, may also be used to monitor the temperature of the tissue or electrode. The return path is provided by a ground pad that is attached to the patient's skin. Some ablation generators for pain management also support bipolar or other multipolar ablation in which the conductive tips of two or more separate monopolar ablation electrodes are placed near each other. One ablation electrode supplies power while another ablation electrode acts as a return. Each ablation electrode requires one channel on the ablation generator. Other arrangements utilize bipolar or other multipolar ablation electrodes.

Examples of ablation generators and ablation systems and methods of making and using the ablation generators and ablation systems can be found at, for example, U.S. Pat. Nos. 8,992,522; 9,039,701; 9,173,676; 9,717,552; 9,956,032; 10,111,703; 10,136,937; 10,136,942; 10,136,943; 10,194,971; 10,342,606; 10,363,063; 10,588,687; 10,631,915; 10,639,098; and 10,639,101; and U.S. Patent Application Publications Nos. 2014/0066917; 2014/081260; 2014/0121658; 2021/0121224; 2021/0236191; 2022/0202484; 2022/0202485; and 2022/0226039 and U.S. Provisional Patent Application Ser. Nos. 63/413,122 and 63/413,133, all of which are incorporated herein by reference in their entireties. In at least some embodiments, these ablation systems can be modified or adapted to perform ablation using short, high voltage pulses, as described herein.

Figure 1:
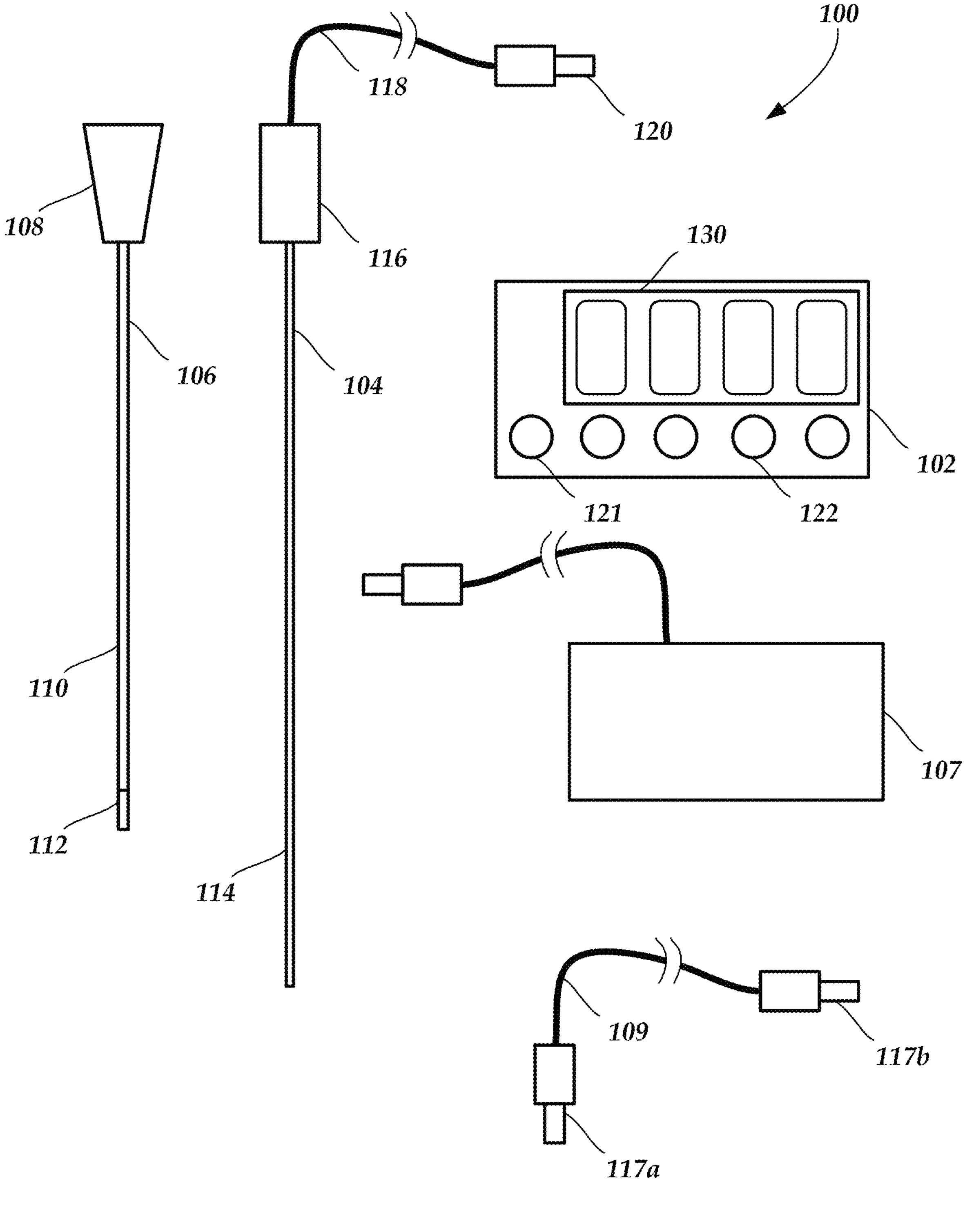
FIG. 1 is a schematic side view of components of one embodiment of an ablation system with a monopolar or monoelectrode ablation electrode.

FIG. 1 illustrates one embodiment of an ablation system 100 that includes an ablation generator 102, one or more monopolar or monoelectrode ablation electrodes 104, one or more cannulas 106, an optional ground pad 107, and one or more optional extension cables 109. In at least some embodiments, each cannula 106 includes a cannula hub 108, an insulated shaft 110, and an active tip 112. The insulated shaft 110 is hollow with a cannula lumen for receiving a monopolar or monoelectrode ablation electrode 104. When inserted into the cannula 106, the monopolar or monoelectrode ablation electrode 104 contacts, and energizes, the active tip 112 of the cannula 106 to produce ablation or electrical stimulation.

In at least some embodiments, the monopolar or monoelectrode ablation electrode 104 includes an electrode shaft 114, an electrode hub 116, a cable 118 that is electrically coupled to the electrode shaft 114, and a connector 120 for connecting to a port 122 of the ablation generator 102 to energize the electrode shaft 114 via the cable 118 and connector 120. The optional adapter or extension 109 includes a cable 109 and connectors 117*a*, 117*b* for coupling the monopolar or monoelectrode ablation electrode 104 to the ablation generator 102. It will be recognized that other ablation systems utilize the monopolar or monoelectrode ablation electrode 104 for ablation instead of, or in addition to, the cannula 106.

The ablation generator 102 can include one or more ports 122 and at least one screen 130. In at least some embodiments, each port 122 is associated with a portion of the screen 130 (or a different screen) and can receive the connector 120 from a monopolar ablation electrode 104. Information such as current, voltage, status, or the like or any combination thereof can be displayed on the screen 130. In at least some embodiments, each port 122 corresponds to an independent channel for operating a monopolar or monoelectrode ablation electrode 104. The ablation generator 102 may also include a ground port 121 for attachment of an optional ground pad 107.

In at least some embodiments, multiple monopolar or monoelectrode ablation electrodes 104 are positioned along the nerve(s) to be ablated. In at least some embodiments, the monopolar ablation electrodes 104 and the ground pad 107 are coupled to the ablation generator 102 to generate ablation lesions sequentially or simultaneously by monopolar ablation. In at least some embodiments, a sequence of ablation periods is performed with two or more lesions generated simultaneously during each ablation period.

Figure 4:
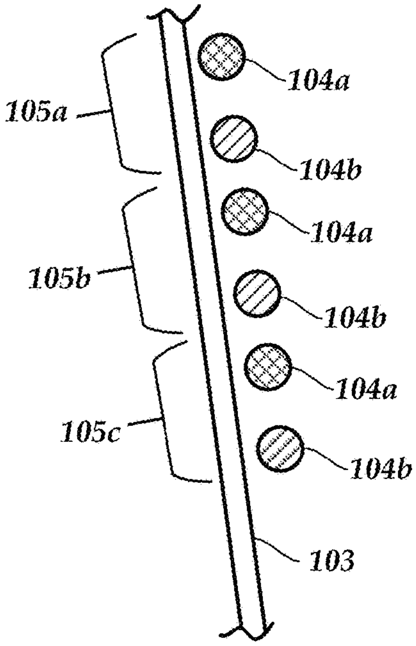
FIG. 4 is a schematic diagram of one embodiment of treating sacroiliac joint pain by ablation of a nerve using an ablation system having multiple monoelectrode ablation electrodes.

In at least some embodiments, the monoelectrode ablation electrodes 104 are used to ablate the nerve(s) in a bipolar manner with monoelectrode ablation electrodes acting as different poles. For example, some of the monoelectrode ablation electrodes 104 are active electrodes and other monoelectrode ablation electrodes are return electrodes. As an example, as illustrated in FIG. 4, the active monoelectrode ablation electrodes 104*a* can alternate with return monoelectrode ablation electrodes 104*b* to ablate different portions of one or more nerves 103. Any other suitable arrangement or assignment of monoelectrode ablation electrodes to different poles can be used.

In at least some embodiments, a separation distance between the monoelectrode ablation electrodes 104*a*, 104*b* is selected to avoid or reduce barotrauma associated with arcing between the monoelectrode ablation electrodes. In at least some embodiments, the ablation system can use multiplexing so that the ablation can occur sequentially for different sets of monopolar or monoelectrode ablation electrodes to allow for positioning the monopolar or monoelectrode ablation electrodes closer together while reducing or avoiding arcing. For example, in the arrangement illustrated in FIG. 4, the ablation system can apply electrical energy to the upper pair 105*a* of monoelectrode ablation electrodes 104*a*, 104*b* and the lower pair 105*c* of monoelectrode ablation electrodes 104*a*, 104*b* simultaneously to ablate the nerve 103. After this ablation, the ablation system can apply electrical energy to the middle pair 105*b* of monoelectrode ablation electrodes 104*a*, 104*b* to ablate the nerve 103 at a medial position. In this manner, arcing between active ablation electrodes 104*a* is reduced as the ablating pairs of ablation electrodes 104*a*, 104*b* are separated by a non-ablating pair of ablation electrodes.

In at least some embodiments, an ablation system can include one or more multipolar ablation electrodes (i.e., a component with two or more electrodes on the same shaft). A multipolar ablation electrode can include two, three, four, or more electrodes. In at least some embodiments, the ablation generator that was previously coupled to monopolar ablation electrodes can be used or adapted for use with one or more multipolar ablation electrodes. It will also be understood that ablation can be performed using any combination of multipolar and monopolar or monoelectrode ablation electrodes.

Figure 2:
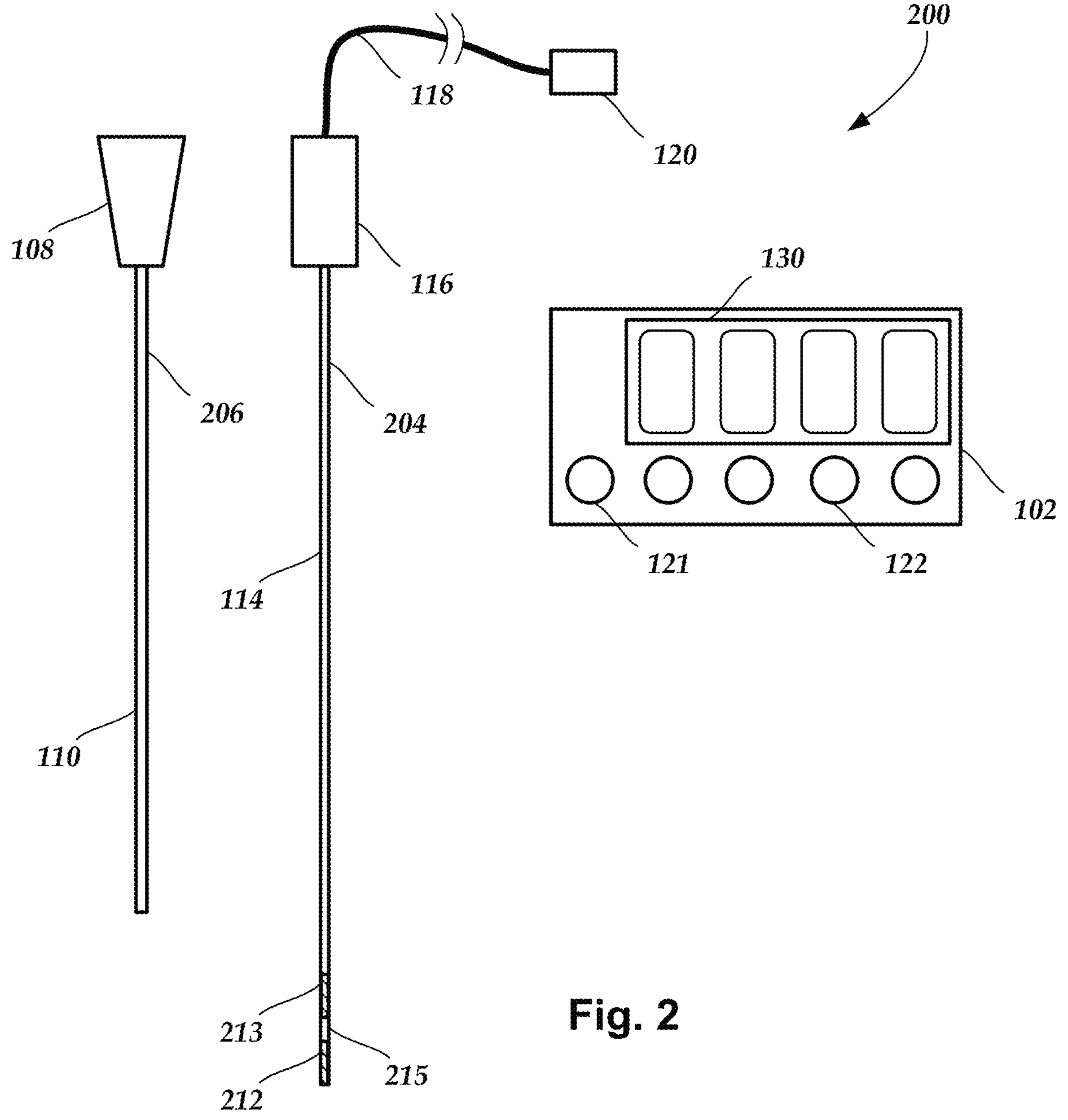
FIG. 2 is a schematic side view of components of one embodiment of an ablation system with a bipolar ablation electrode.

FIG. 2 illustrates one embodiment of an ablation system 200 that includes an ablation generator 102, a multipolar ablation electrode 204, and a cannula 206. In the illustrated embodiment of FIG. 2, the multipolar ablation electrode 204 is a bipolar ablation electrode. It will be recognized that some embodiments of an ablation system can include more or fewer components.

The cannula 206 includes a cannula hub 108 and a cannula shaft 110. The cannula shaft 110 is hollow for receiving the multipolar ablation electrode 204. The multipolar ablation electrode 204 includes an electrode shaft 114, a first electrode element 212, a second electrode element 213, an insulative material 215 (which may be part of the electrode shaft) separating the first and second electrode elements, an electrode hub 116, a cable 118 that is electrically coupled to the electrode shaft 114, and a connector 120 for coupling to at least one port 122 of the ablation generator 102 to energize the first electrode element 212 or second electrode element 213 (or both) via the cable 118 and connector 120. (The term "electrode element" is used for clarity when the electrode elements are part of a multipolar electrode. An "electrode element" is an electrode.) In at least some embodiments, the length of the insulative material 215 or the separation distance between the first and second electrode elements 212, 213 is at least 4, 5, or 6 mm. In at least some embodiments, a separation distance between the first and second electrode elements 212, 213 is selected to avoid or reduce barotrauma associated with arcing between the first and second electrode elements. It will be understood that other multipolar ablation electrodes 204 can include three, four, five, six, or more electrode elements. Each adjacent pair of electrode elements of a multipolar ablation electrode 204 is separated by insulative material 215.

Figure 3:
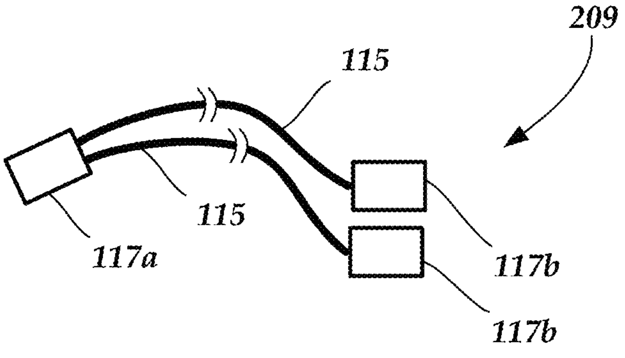
FIG. 3 is a schematic side view of components of one embodiment of an adapter for coupling a bipolar ablation electrode to an ablation generator.

Returning to FIG. 3, the multipolar ablation electrode 204 has conductors that extend along the cable 118, optionally through the electrode shaft 114. Each conductor couples to one or more of the electrode elements, such as the first electrode element 212 or the second electrode element 213. In at least some embodiments, a separate conductor is provided for each electrode element. In at least some embodiments, at least one of the conductors is electrically coupled to one or more of the electrode elements (for example, electrode element 212) and supplies power to that electrode element and at least one other of the conductors is electrically coupled to the one or more other electrode elements (for example, electrode element 213) and acts as a return. In at least some embodiments, user selection at the ablation generator 102 determines which electrode elements are active electrodes and which electrode elements are return electrodes. In at least some embodiments, this user selection may be modified. In at least some embodiments, the assignment of an electrode element as an active electrode or a return electrode may change during operation of the ablation generator 102.

At least some ablation generators provide a single channel at each port 122. In at least some embodiments, the multipolar ablation electrode 204 uses a separate channel for each of the electrode elements, such as the first and second electrode elements 212, 213. In at least some embodiments, multiple electrode elements may be coupled to the same port 122 so that these electrode elements are either active electrodes or return electrodes simultaneously. In at least some embodiments, the ablation system 200 can include an adapter 209, illustrated in FIG. 3, with a connector 117*a* to connect to the connector 120 of the multipolar ablation electrode 104, two or more cables 115 that are individually coupled through the connector 117*a* to a different one of the conductors of the bipolar ablation electrode, and two or more port connectors 117*b* for coupling to individual ports 122 of the ablation generator 102. This permits one or more of the ports 122 to energize some of the electrode elements (for example, electrode element 212) and one or more other ports 122 to act as a return using one or more of the other electrode elements (for example, electrode element 213).

Figure 5:
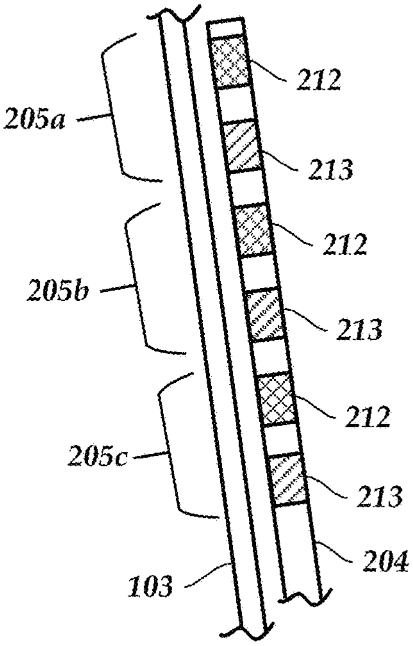
FIG. 5 is a schematic diagram of one embodiment of treating sacroiliac joint pain by ablation of a nerve using an ablation system having a single multipolar ablation electrode.
Figure 6:
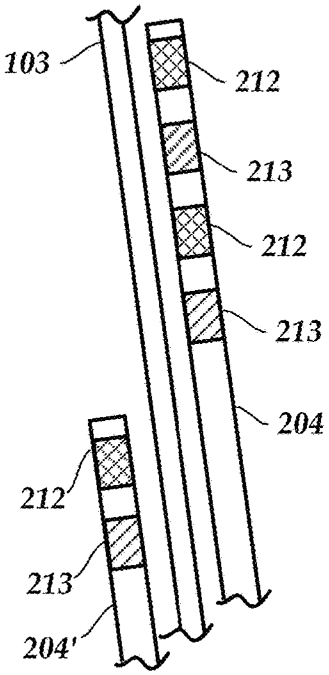
FIG. 6 is a schematic diagram of one embodiment of treating sacroiliac joint pain by ablation of a nerve using an ablation system having multiple multipolar ablation electrodes.

FIG. 5 illustrates a multipolar ablation electrode 204 with six electrode elements 212, 213. In at least some embodiments, the electrode elements 212, 213 are grouped in pairs that each include a first electrode element 212 and a second electrode element 213. Any other suitable arrangement of the electrode elements into pairs, triplets, or larger sets can be used. In addition, the arrangement can be alternating between first and second electrode elements 212, 213, as illustrated in FIG. 5, or any other suitable arrangement of the electrode elements of a set. In at least some embodiments, the ablation system can include multiple multipolar electrode elements 204, 204', as illustrated in FIG. 6.

In at least some embodiments, the ablation system can use multiplexing so that ablation can occur sequentially for different sets of electrode elements 212, 213 to allow for positioning the electrode elements 212, 213 closer together. For example, in the arrangement illustrated in FIG. 5, the ablation system can apply electrical energy to the upper pair 205*a* of electrode elements 212, 213 and the lower pair 205*c* of electrode elements 212, 213 simultaneously to ablate the nerve. After this ablation, the ablation system can apply electrical energy to the middle pair 205*b* of electrode elements 212, 213 to ablate the nerve at a medial position. In this manner, arcing between active electrodes is reduced as they are separated by an inactive pair of electrodes.

Nerve ablation can be used to treat pain associated with the sacroiliac (SI) joint pain or other lower back pain including, for example, chronic axial low back pain with confirmed Modic type I or II changes. Such treatments can include ablation of spinal nerves that extend from the spinal cord in the range of the sacral or lumbar vertebrae including, but not limited to, the S1-S4 and L3-L5 vertebrae. In at least some embodiments, the SI joint pain is treated by SI joint denervation by ablating one or more (or all) of the sacral lateral branch nerves innervating the SI joint. In at least some embodiments, the treatment may also include facet joint denervated by ablating the medial branch of a target vertebral level (for example, L4, L5, or S1) and the medial branch of the level above the target vertebral level.

Conventionally, one or more nerves is typically ablated using radiofrequency (RF) energy. In many instances, multiple sites along one or more nerves are ablated to create ablation lesions. Often, these lesions are connected. Conventional ablation treatments typically include thermally ablating the nerve with radiofrequency (RF) energy; however, the delivered energy is controlled to prevent or reduce thermal damage to other tissues, such as the spinal cord or other nearby nerves or tissue. Accordingly, RF-based ablation treatment can require a substantial amount of time to be effective. Such time is typically at least 1-3 minutes or more per ablation site. RF-based ablation treatments may also be time consuming to assure that ablation electrodes are properly positioned and the ablation lesions are fully connected. Local tissue electrical properties (including the properties of fat near the nerves) may hinder the creation of bipolar ablation lesions and reduce the efficacy of the procedure.

In contrast to conventional thermal ablation, short, high voltage pulses can be used for nerve ablation to treat SI joint pain or other lower back pain. Using short, high voltage pulses can reduce the procedure time and create continuous lesions with only seconds of application of the pulses. Although no particular theory is necessary for practicing the invention, it is believed that the short, high voltage DC pulses, which can generate locally high electric fields, cause electroporation of the nerve cells. This results in disruption of the cell by generating pores in the cell membrane. The electroporation of the nerve cells produces irreversible damage that results in cell death or destruction. It is believed that, if the applied electric field at the membrane is larger than a threshold value, the electroporation is irreversible and the pores remain open. This allows exchange of material across the membrane and leads to necrosis or cell death.

Because the high voltage pulses are applied for a much shorter time (for example, in a window of no more than 10 seconds), the total amount of localized heating can be much less than for the conventional RF-based nerve ablation. Accordingly, damage to other surrounding tissue is avoided or substantially reduced. This is particularly important for nerve ablation due to the proximity of the ablated nerves to the spinal cord and other nerves.

Nerve cells are particularly resistant to electroporation. In at least some instances, the nerve cells have a higher threshold to electroporation and require a higher electric field (in at least some embodiments, at least 3800 V/cm) to electroporate than other cells. For example, in at least some instances, the nerve cells require at least nine times the electric field to electroporate than myocardial cells or at least twice the electric field to electroporate than red blood cells, vascular smooth muscle cells, or endothelial cells. There may be concern regarding the use of such high voltage pulses near the spinal cord or other sensitive tissues. In at least some embodiments, the size of the irreversible ablative zone of the electric field can be managed (for example, through electrode design or ablation parameters) for irreversible ablation of the target nerve but not surrounding structures.

In at least some embodiments, the voltage of the pulses is at least 1, 1.5, 2, 2.5, 3, 3.5, 3.8, 4, 4.5, or 5 kV. In at least some embodiments, the pulses generate an electric field of at least 3.5, 3.8, 4, 4.5, or 5 kV/cm. In at least some embodiments, a time window for delivery of a treatment set of short, high voltage DC pulses is no more than 100, 150, 200, 250, 300, 500, or 750 milliseconds or 1, 2, or 5 seconds. In at least some embodiments, a single treatment set of short, high voltage DC pulses is sufficient for nerve ablation. In other embodiments, two, three, four, five, or more treatment sets of short, high voltage DC pulses are used for the nerve ablation. In at least some embodiments, the time between treatment sets is at least 1, 2, 5, 10, 20, 30, 45, or more seconds and may be measured in minutes or may be longer. In at least some embodiments, the time between treatment sets may allow for heat dissipation or to charge the capacitors of the ablation generator or any combination thereof.

A treatment set of pulses includes multiple pulses that are delivered during the treatment time window. The pulses can be monophasic, biphasic, or multiphasic. In at least some embodiments, an interphase time delay for a biphasic or multiphasic pulse is no longer than the duration of one phase of the pulse. In at least some embodiments, the time duration for each of the pulses is no more than 0.5, 1, 5, 10, 20, 50, 100, 200, or 500 nanoseconds or 1, 5, 10, 20, 50, 100, 200, 300, or 500 microseconds. In at least some embodiments, the time duration of each of the pulses is at least 0.5, 1, 5, 10, 20, 50, 100, 200, or 500 nanoseconds or 1, 5, 10, 20, 50, 100, 200, or 300 microseconds. The number of pulses in a treatment set of pulses may be at least 10, 20, 50, 100, 200, 500, 1000 or more.

In at least some embodiments, the pulses are rectangular or any other suitable pulse shape. In at least some embodiments of rectangular or other pulses, the rise or fall periods of the pulse may not result in sharp increases/decreases. Such rise or fall periods may be used to, for example, manage overshoot or ringing effects.

In at least some embodiments, the pulses can be arranged in pulse bursts with each pulse burst containing at least 2, 5, 10, 15, 20, 25, 30, 40, 50, 100, or more pulses. The pulses of the pulse burst are separated from each other by a period that, at least in some instances, is no more than 1, 10, 50, 100, 200, 500, or 1000 microseconds. In at least some embodiments, the pulses of a pulse burst (or pulses that are not in a pulse burst arrangement) are separated from each other by at least 0.5, 1, 10, 20, 50, 100, 200, or 500 microseconds. In at least some embodiments, the pulses of a pulse burst (or pulses that are not in a pulse burst arrangement) are separated from each other by no more than 1, 10, 20, 50, 100, 200, 500, or 1000 microseconds. In some embodiments, each of the pulses in a pulse burst are identical in phase, identical in duration, or both. In other embodiments, at least two of the pulses differ from each other in the number of phases, duration, or both.

In at least some embodiments, the time window includes multiple pulse bursts, for example, at least 2, 4, 5, 10, or more pulse bursts. In some embodiments, each of the pulses bursts is identical in the number of pulses, the period between pulses, or both. In other embodiments, at least two of the pulse bursts may differ from each other in the number of pulses, the period between pulses, or both.

In at least some embodiments, the pulse bursts are separated from each other by a burst period that, at least in some instances, is no more than 3, 10, 50, 100, 200, 500, or 1000 microseconds and is at least 3, 10, 50, 100, 200, or 500 microseconds. In at least some embodiments, the burst period is at least 3, 4, 5, or 10 times longer than the period between the individual pulses of a burst.

In at least some embodiments, there may be higher levels of aggregation of pulses or pulse bursts. U.S. Pat. No. 10,709,502, incorporated herein by reference in its entirety, discloses examples of pulse arrangements for tissue ablation.

In at least some embodiments, the values for the delivery parameters described above are selected based on one or more factors such as, for example, efficacy, treatment duration, treatment outcomes, patient pain, damage to tissues other than the SI joint, tissue heating, generation of bubbles in body fluids, skeletal muscle stimulation, arcing, tissue aggregation, or the like or any combination thereof.

In at least some embodiments, one or two ablation electrodes 104/204 are inserted into the body of the patient and positioned near the nerve(s) to be ablated. In at least some embodiments, the ablation electrode(s) 104/204 is/are positioned at a particular distance away from the spinal cord 448 to avoid hearing or damage to the spinal cord.

After insertion of the ablation electrode(s) 104/204, short, high voltage pulses are then applied to the nerve(s) to form ablation lesions, as described above. After treatment, the ablation electrode(s) 104/204 are removed from the patient's body.

Figure 7:
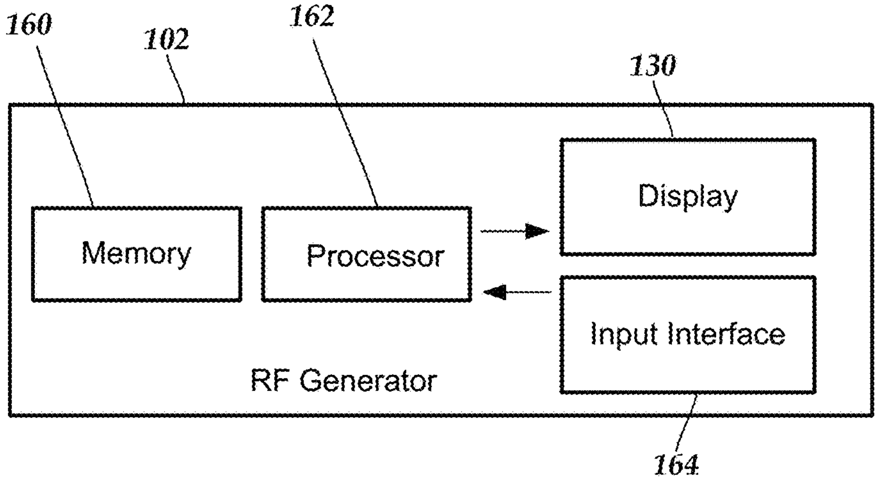
FIG. 7 is a block diagram of one embodiment of an ablation generator.

FIG. 7 illustrates one embodiment of an ablation generator 102 that includes a memory 160, a processor 162, a display 130, and an input interface 164. It will be understood that any of these components or combination of components can be provided as part of another device that is coupled, or coupleable, to the ablation generator 102. The processor 162 can include any suitable processor including one or more hardware processors that may be local to the user or non-local to the user or other components of the computer. The processor 102 is configured to execute instructions provided to the processor.

Any suitable memory 160 can be used. The memory 160 illustrates a type of computer-readable media, namely computer-readable storage media. Computer-readable storage media may include, but is not limited to, nonvolatile, non-transitory, removable, and non-removable media implemented in any method or technology for storage of information, such as computer readable instructions, data structures, program modules, or other data. Examples of computer-readable storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computer.

Communication methods provide another type of computer readable media; namely communication media. Communication media typically embodies computer-readable instructions, data structures, program modules, or other data in a modulated data signal such as a carrier wave, data signal, or other transport mechanism and include any information delivery media. The terms "modulated data signal," and "carrier-wave signal" includes a signal that has one or more of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, and other wireless media.

The memory 160 can have instructions stored thereon. The instructions, when executed by the processor 162 can perform actions. Such actions can include, for example, applying pulses to the ablation electrode to ablate the sacroiliac joint nerve within the vertebral body. The instructions may include parameter values, such as pulse duration, pulse voltage, the electric field generated by the pulses, the number of pulses, the separation time between pulses, the number of pulse bursts, the number of pulses in a pulse burst, the separation time between pulse bursts, and the like or any combination thereof.

The display 130 can be any suitable display, such as a monitor, screen, display, or the like. The input interface 164 can be, for example, keys, a touchpad, a keyboard, a mouse, a touch screen, a track ball, a joystick, a voice recognition system, another device that is in communication with the ablation generator 102, or any combination thereof, or the like and can be used by the user to interact with a user interface of the ablation generator 102.

The input interface 164 allows a user to program or alter parameter values of the ablation generator 102 for delivery of the short, high voltage pulses, as described herein. In at least some embodiments, the user can program the ablation generator 102 prior to a procedure. In at least some embodiments, the user can input or alter parameter values during a procedure.

The above specification provides a description of the structure, manufacture, and use of the invention. Since many embodiments of the invention can be made without departing from the spirit and scope of the invention, the invention also resides in the claims hereinafter appended.

What is claimed as new and desired to be protected is:

1. A method to treat sacroiliac joint pain, the method comprising inserting at least one ablation electrode into a patient to ablate at least one spinal nerve extending from the spinal cord in the vertebral range of the lumbar vertebrae L3, L4, or L5 or any of the sacral vertebrae; and applying pulses to the at least one ablation electrode to ablate the at least one spinal nerve, wherein each of the pulses has a duration of no more than 300 microseconds and at least some of the pulses have a voltage of at least 1 kV.

2. The method of claim 1, wherein the at least one spinal nerve comprises at least one sacral lateral branch nerve.

3. The method of claim 1, wherein each of the pulses has a voltage of at least 2 kV.

4. The method of claim 1, wherein each of the pulses has a voltage of at least 3 kV.

5. The method of claim 1, wherein at least a plurality of the pulses each have a duration of no more than 100 microseconds.

6. The method of claim 1, wherein at least a plurality of the pulses are separated from each other by no more than 20 milliseconds.

7. The method of claim 1, wherein the pulses are arranged in a plurality of pulse bursts, wherein each of the pulse bursts comprises a plurality of the pulses, wherein the pulse bursts are separated from each other by at least 3 microseconds.

8. The method of claim 1, wherein the pulses are monophasic.

9. The method of claim 1, wherein the pulses are multiphasic.

10. The method of claim 1, wherein the at least one spinal nerve comprises a plurality of the spinal nerves and inserting the at least one ablation electrode comprises inserting the at least one ablation electrode at different positions along the plurality of the spinal nerves.

11. The method of claim 1, wherein the at least one ablation electrode comprises a plurality of monoelectrode ablation electrodes.

12. The method of claim 11, wherein applying the pulses comprises applying the pulses to at least one set of the monoelectrode ablation electrodes, wherein each of the at least one set comprises at least one first monoelectrode ablation electrode that is an active electrode and at least one second monoelectrode ablation electrode that is a return electrode.

13. The method of claim 1, wherein the at least one ablation electrode comprises at least one multipolar ablation electrode.

14. A method to treat sacroiliac joint pain, the method comprising inserting at least one ablation electrode into a patient to ablate at least one spinal nerve extending from the spinal cord in the vertebral range of the sacral vertebrae or the lumbar vertebrae L3, L4, or L5; and applying pulses to the at least one ablation electrode to ablate the at least one spinal nerve, wherein each of the pulses has a duration of no more than 300 microseconds and at least some of the pulses generate an electric field of at least 3 kV/cm.

15. The method of claim 14, wherein each of the pulses generates an electric field of at least 3.5 kV/cm.

16. The method of claim 14, wherein at least a plurality of the pulses each have a duration of no more than 100 microseconds.

17. The method of claim 14, wherein at least a plurality of the pulses are separated from each other by no more than 20 milliseconds.

18. The method of claim 14, wherein the at least one ablation electrode comprises a plurality of monoelectrode ablation electrodes.

19. The method of claim 18, wherein applying the pulses comprises applying the pulses to at least one set of the monoelectrode ablation electrodes, wherein each of the at least one set comprises at least one first monoelectrode ablation electrode that is an active electrode and at least one second monoelectrode ablation electrode that is a return electrode.

20. The method of claim 14, wherein the at least one ablation electrode comprises at least one multipolar ablation electrode.

* * * * *